(12) United States Patent
Hargrave et al.

(10) Patent No.: US 7,749,179 B2
(45) Date of Patent: Jul. 6, 2010

(54) DEVICE FOR STABILIZING AN ARM

(75) Inventors: David C. Hargrave, Madison, NJ (US); Nick Grippi, Butler, NJ (US); John W. Sperling, Rochester, MN (US); Robert H. Cofield, Rochester, MN (US); David Veltre, Cedar Grove, NJ (US)

(73) Assignee: DJO, LLC, Vista, CA (US)

( * ) Notice: Subject to any disclaimer, the term of this patent is extended or adjusted under 35 U.S.C. 154(b) by 0 days.

(21) Appl. No.: 11/282,330

(22) Filed: Nov. 18, 2005

(65) Prior Publication Data

US 2006/0258966 A1 Nov. 16, 2006

Related U.S. Application Data

(60) Provisional application No. 60/681,116, filed on May 13, 2005.

(51) Int. Cl.
*A61F 5/00* (2006.01)
*A45F 3/14* (2006.01)

(52) U.S. Cl. .......................................... 602/4; 224/157

(58) Field of Classification Search ......... 128/845–846, 128/878–879, 869, 881; 602/4, 5, 1; 5/89; 294/140, 152, 156; 224/157, 158
See application file for complete search history.

(56) References Cited

U.S. PATENT DOCUMENTS

| 3,103,216 | A | * | 9/1963 | Scott .............................. 602/4 |
| 4,198,964 | A | | 4/1980 | Honneffer |
| 4,220,149 | A | | 9/1980 | Mims, Jr. |
| 4,232,664 | A | | 11/1980 | Blatt |
| 4,372,301 | A | | 2/1983 | Hubbard et al. |
| 4,437,459 | A | | 3/1984 | Slavetskas |
| 4,480,637 | A | | 11/1984 | Florek |
| 4,564,008 | A | | 1/1986 | Donahoo |
| 4,622,961 | A | | 11/1986 | Christensen |
| 4,625,719 | A | | 12/1986 | Chambers |
| 4,759,353 | A | | 7/1988 | Melendez et al. |
| 4,834,082 | A | | 5/1989 | Ghadiali |
| 5,334,132 | A | * | 8/1994 | Burkhead ..................... 602/4 |
| 5,413,552 | A | | 5/1995 | Iwuala |
| RE35,028 | E | * | 8/1995 | Casebolt et al. ............. 119/857 |
| 5,464,383 | A | | 11/1995 | Padden et al. |
| 5,569,172 | A | | 10/1996 | Padden et al. |
| 5,772,617 | A | * | 6/1998 | Lay .............................. 602/4 |
| 5,792,083 | A | | 8/1998 | Joslin |
| 5,830,165 | A | | 11/1998 | Rowe et al. |
| 6,095,993 | A | | 8/2000 | Hawkins |
| 6,099,489 | A | | 8/2000 | Herzberg et al. |
| 6,102,877 | A | | 8/2000 | Joslin |
| 6,659,971 | B2 | * | 12/2003 | Gaylord ........................ 602/4 |
| 6,770,044 | B1 | | 8/2004 | Joslin |
| 7,189,213 | B1 | * | 3/2007 | Weber ......................... 602/20 |
| 7,244,239 | B2 | * | 7/2007 | Howard ........................ 602/4 |

(Continued)

FOREIGN PATENT DOCUMENTS

AU          718108          4/2000

*Primary Examiner*—Patricia Bianco
*Assistant Examiner*—Tarla R Patel
(74) *Attorney, Agent, or Firm*—Ropes & Gray LLP

(57) ABSTRACT

The invention provides, in various embodiments, devices and methods for supporting an injured arm. In certain embodiments, the invention relates to adjustable sling assemblies.

46 Claims, 16 Drawing Sheets

U.S. PATENT DOCUMENTS

2003/0135141 A1 7/2003 Berhorst
2003/0187373 A1* 10/2003 Gaylord .................. 602/4
2005/0010147 A1* 1/2005 Kazmierczak et al. ......... 602/4
2005/0020950 A1 1/2005 Jestrabek-Hart

* cited by examiner

DEVICE FOR STABILIZING AN ARM

REFERENCE TO RELATED APPLICATIONS

This application claims the benefit of U.S. Provisional Patent Application Ser. No. 60/681,116, filed on May 13, 2005, the specification of which is incorporated by reference herein in its entirety.

BACKGROUND OF THE INVENTION

Many attempts have been made to provide stabilizing arm slings which comfortably and adjustably support a patient's arm and which hold the sling against the body to limit unintentional movement of the arm and/or the shoulder. Many available slings not configured to allow the patient to readily adjust the fit of the sling but require either the physician or another person to remove or adjust the sling. Moreover, when a patient desires to remove such slings for performing rehabilitation exercises or for other purposes during treatment the patient must typically remove the sling entirely, such that when the sling is reapplied the sling length settings must be re-adjusted.

Early attempts at securing slings against the body involved extending and securing a separate belt across an outer surface of the sling, around the upper arm of the arm to be immobilized and under the opposite arm. Such an arrangement often proved uncomfortable and difficult to attach.

There remains a need for a stabilizing arm sling which comfortably secures an arm in the sling against the body and which is easy to put on and adjust.

SUMMARY OF THE INVENTION

The invention addresses various deficiencies in the art by providing, in various embodiments, a sling assembly with improved ergonomic features for supporting an injured arm. According to various aspects, the sling assembly includes a pouch for receiving a patient's arm and which adjustably connects to one or more straps that fit the pouch to the patient's torso and are of adjustable length.

According to one exemplary implementation, the invention provides a sling assembly that includes a pouch having a distal portion near the region of a user's wrist and a proximal portion near the region of the patient's elbow. The pouch includes an inside panel, an outside panel and a shoulder strap having a first end and a second end. The first end of the shoulder strap attaches to the distal portion of the pouch, and the second end of the shoulder strap attaches to the proximal portion of the pouch. The sling also includes a locking strap having a front end and a back end. The front end of the locking strap attaches to the shoulder strap near the first end, and the back end of the locking strap attaches to the shoulder strap intermediate to the front end of the locking strap and the second end of the shoulder strap. In certain exemplary embodiments, the shoulder and locking straps are adjustable, having tabs or other features that form a Velcro, hook and loop or other mechanical connection to the sling assembly. In certain embodiments, the sling assembly includes one or more locking assemblies to form the connections between the pouch and the straps.

In one exemplary embodiment, a sling is provided with a pouch for receiving and supporting a patient's arm. The pouch has a distal portion near the region of the user's wrist, a proximal portion near the region of the user's elbow, a front panel and a back panel. The sling assembly further includes a shoulder strap having a front portion and a rear portion, and a locking strap having a front portion and a rear portion adapted to extend under the user's arm and connect with the shoulder strap at a position along the user's back. The sling further includes a locking assembly adapted to connect the front portion of the locking strap to the distal portion of the pouch and to the front portion of the shoulder strap.

According to another exemplary embodiment, the invention provides a sling having a pouch for receiving and supporting a patient's arm. The pouch has a distal portion near the region of the user's wrist, a proximal portion near the region of the user's elbow, and a front panel and a back panel. The sling includes a shoulder strap having a front portion and a rear portion, and a locking assembly adapted to attach the shoulder strap to the front panel and the back panel of the pouch through one or more tabs. According to such an exemplary embodiment, at least one of the one or more tabs is disengagable from and re-attachable to the locking assembly so as to disengage at least one panel from the locking assembly without disengaging the other panel from the locking assembly.

According to another exemplary embodiment, a sling is provided with a pouch for receiving and supporting a patient's arm, and the pouch has an elastic component (or may be substantially elastic) and an inelastic strip positioned along a bottom region of the pouch. A shoulder strap is provided and configured to attach to the front and back panels and support the weight of the user's arm.

According to one aspect, the sling assembly includes a locking assembly adapted to attach the shoulder strap to the front and back panels of the pouch. The locking assembly attaches to the front panel of the pouch through one or more tabs on the front panel. The tabs may be disengagable and re-attachable from the locking assembly so as to allow one or both of the panels to open downward (away from the user's torso if the front panel is opened, and toward the user's torso if the back panel is opened) to allow the patient to remove the arm from the sling to perform rehabilitation or for other purposes. According to one implementation, a tab connecting the front panel may be disengaged from the locking assembly without disengaging the back panel from the locking assembly, thereby retaining the connection between the back panel and the shoulder strap. Similarly, the tab connecting the back panel may be disengaged from the locking assembly without disengaging the front panel from the locking assembly, thereby retaining the connection between the front panel and the shoulder strap.

According to various implementations, the locking assembly of the sling assembly includes one or more buckle assemblies, such as a D-ring buckle assembly, adapted to receive one or more connecting tabs on the pouch and connect the pouch to the straps. The locking assembly may also include one or more latches, tabs and other mechanical fasteners that connect the locking strap to the shoulder strap in one or more locations, and connect the shoulder strap to the pouch, and connect the locking strap to the pouch and/or to the shoulder strap. The connections between straps and pouch are movable and adjustable by the patient.

According to another exemplary implementation, the sling assembly includes an abduction pillow or other support pad for providing ergonomic support for the patient. The support pad includes a first surface for resting against the user's torso, a second surface facing away from the user's torso and for supporting the pouch, a top surface, and a bottom surface. The support pad may be configured so that the bottom surface of the support pad is wider than the top surface of the support pad, such that the second surface angles away from the user's torso. The support pad may also include a stabilizing strap attached to the first or second surface of the support pad and configured to extend across the pouch and attach to the front panel.

According to another implementation, the pouch of the sling assembly may include one or more hand straps attached to an interior face of a panel on the distal end of the pouch. The hand straps may be positioned to fit between a patient's thumb and forefinger when the sling is applied to the arm. Accordingly to another aspect, the sling assembly may be configured to be interchangeable from the patient's right arm to the left.

These and other features and advantages of the invention are described in further detail below with regard to illustrative embodiments of the invention.

BRIEF DESCRIPTION OF THE DRAWINGS

The foregoing and other objects and advantages of the invention will be appreciated more fully from the following further description thereof, with reference to the accompanying drawings wherein.

DESCRIPTION OF ILLUSTRATIVE EMBODIMENTS

To provide an overall understanding of the invention, certain illustrative embodiments will now be described. However, it will be understood by one of ordinary skill in the art that the systems and methods described herein can be adapted and modified for other suitable applications and that such other additions and modifications will not depart from the scope hereof. Therefore, specific structural and functional details disclosed herein are not to be interpreted as limiting, but merely as a basis for the claims and as a representative basis for teaching one skilled in the art to variously employ the invention in virtually any appropriately detailed structure.

Figure 1:
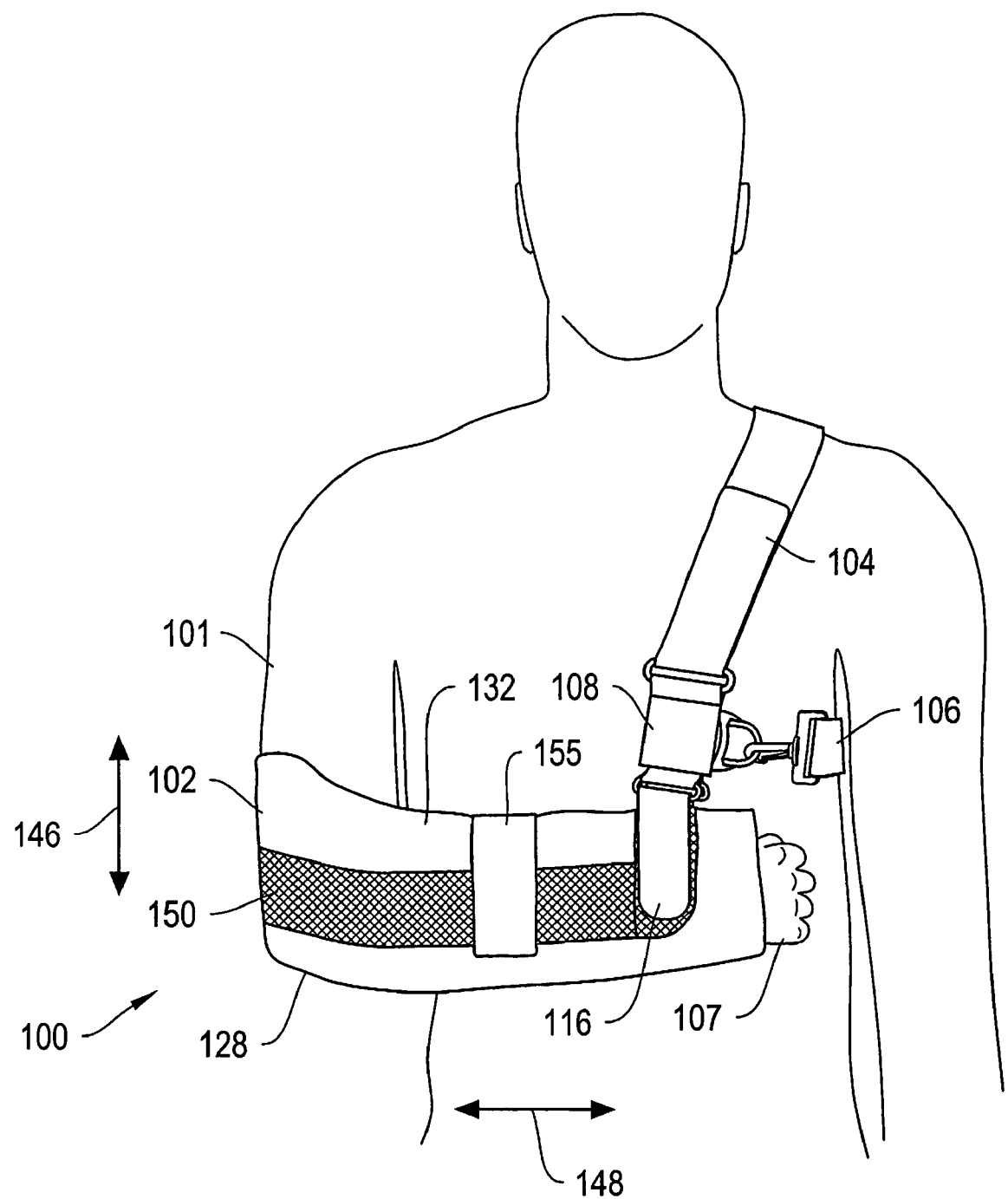
FIG. 1 depicts one embodiment of a sling assembly, according to an illustrative embodiment of the invention.

Referring to the drawings in more detail, FIG. 1 refers to an illustrative embodiment of a sling assembly 100 that supports the arm 101 of a patient. More particularly, the arm sling assembly 100 of FIG. 1 includes a sling pouch 102 that is fitted to the patient's right arm, a shoulder strap 104 that extends over the patient's left shoulder, a locking strap 106 that extends and under the patient's left arm and behind the patient to adjoin the shoulder strap 104 behind the patient, and a locking assembly 108 located distally with respect to the pouch 102 and adapted to connect the pouch 102 and the straps 104 and 106.

Figure 7:
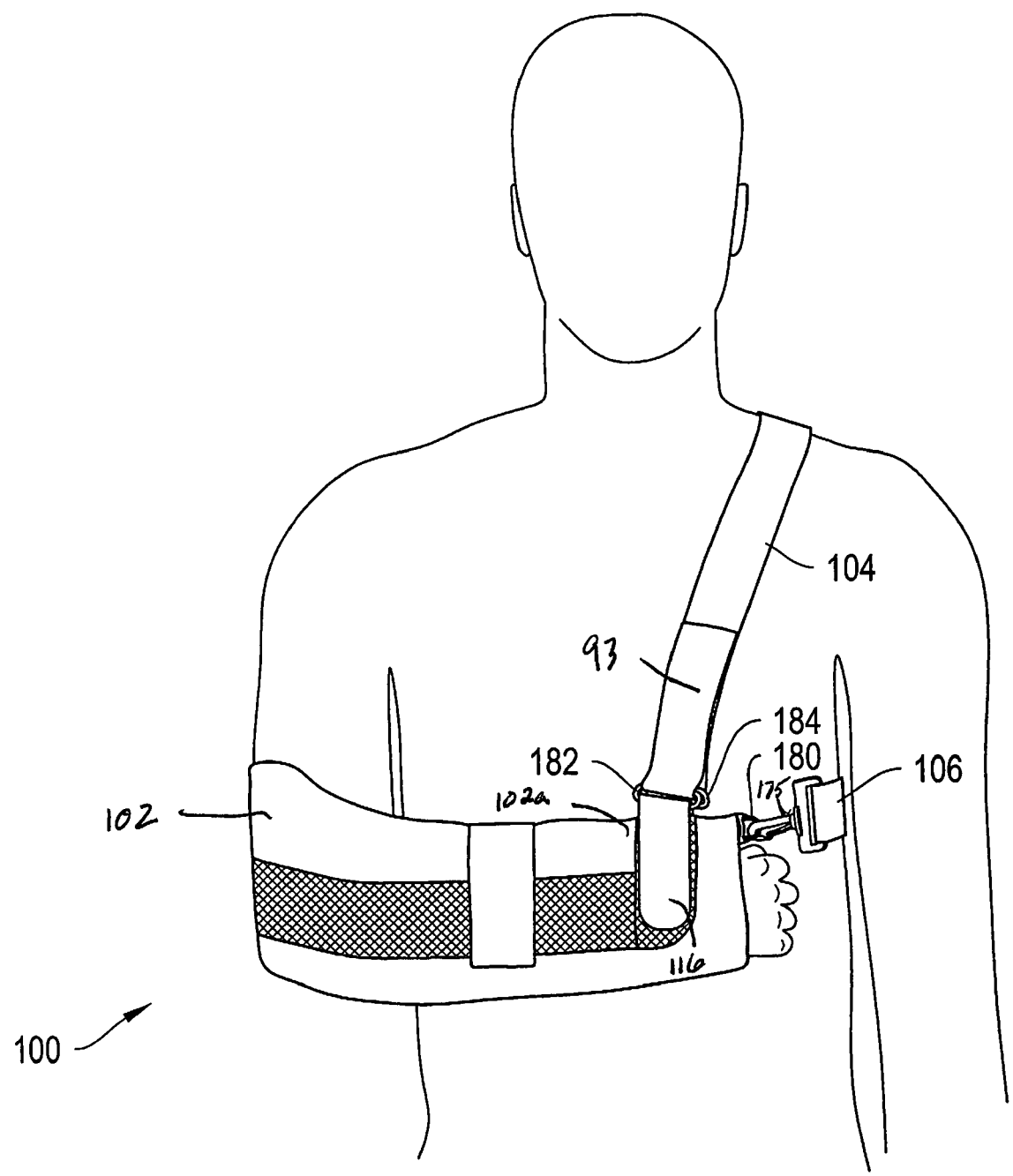
FIG. 7 depicts an exemplary locking assembly that may be used to connect the pouch to one or more straps.

The sling pouch 102 may be formed from a sheet of cloth cut to shape and folded in half along a bottom edge 128 of the sling pouch 102 so as to form a first or front panel 132, also referred to as an outside panel, and a second or back panel 134, also referred to as an inside panel. The pouch 102 has a distal portion 102a (as shown in FIG. 7) near the region of the user's wrist, and a proximal region near the region of the user's elbow.

The pouch 102 of the depicted sling assembly 100 connects with the shoulder strap 104, which extends from the distal portion of the pouch 102 and over the shoulder of the patient's non-injured arm. The pouch 102 also connects with the locking strap 106, which travels under the patient's non-injured arm and around the patient's back and connects to the reverse side 105 of the shoulder strap 104. In the depicted embodiment, the connections between the pouch 102 and the straps 104 and 106 are formed through the locking assembly 108. As described more particularly below with reference to FIGS. 3A, 4A, 6 and 7, the pouch 102 connects at its distal portion to the locking assembly 108 through tabs 116 and 117, which are positioned on the front 132 and back 134 panels of the pouch 102.

The exemplary sling assembly 100 also includes a stabilizing strap 155, which wraps over a top portion of the pouch 102 and adjoins panel 132 to panel 134, thereby securing the pouch 102 around the patient's forearm and stabilizing the forearm. In one exemplary configuration, the strap 155 is sewn to a top portion of the flap 134, while in other embodiments an end of the stabilizing strap 155 is sewn or otherwise fixed to a portion of a support pad, such as an abduction pillow (shown below), that is placed between the sling and the patient's torso. In such embodiments, the strap 155 wraps over the user's forearm and adjustably affixes through a Velcro, hook and loop or other suitable connection to the joining strip 150 which is located on the flap 132.

Figure 2A:
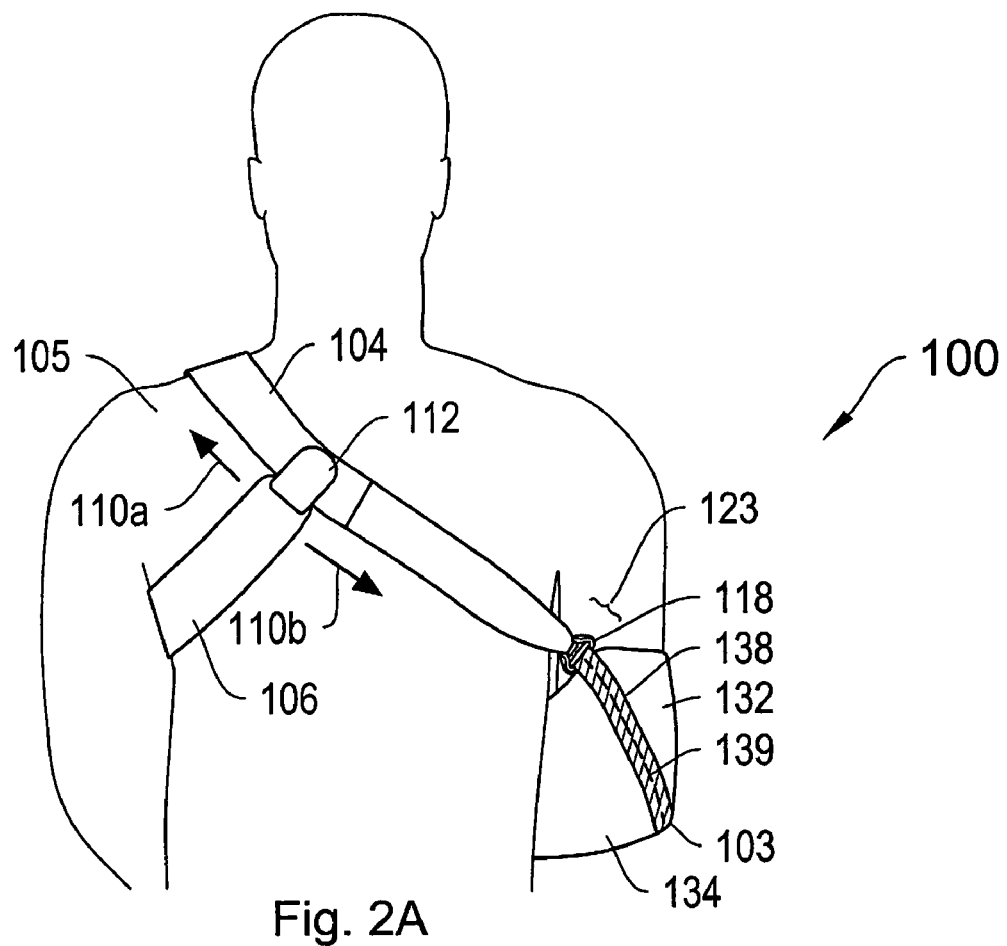
FIGS. 2A-2B depict a rear view of exemplary embodiments of the sling assembly shown in FIG. 1.
Figure 2B:
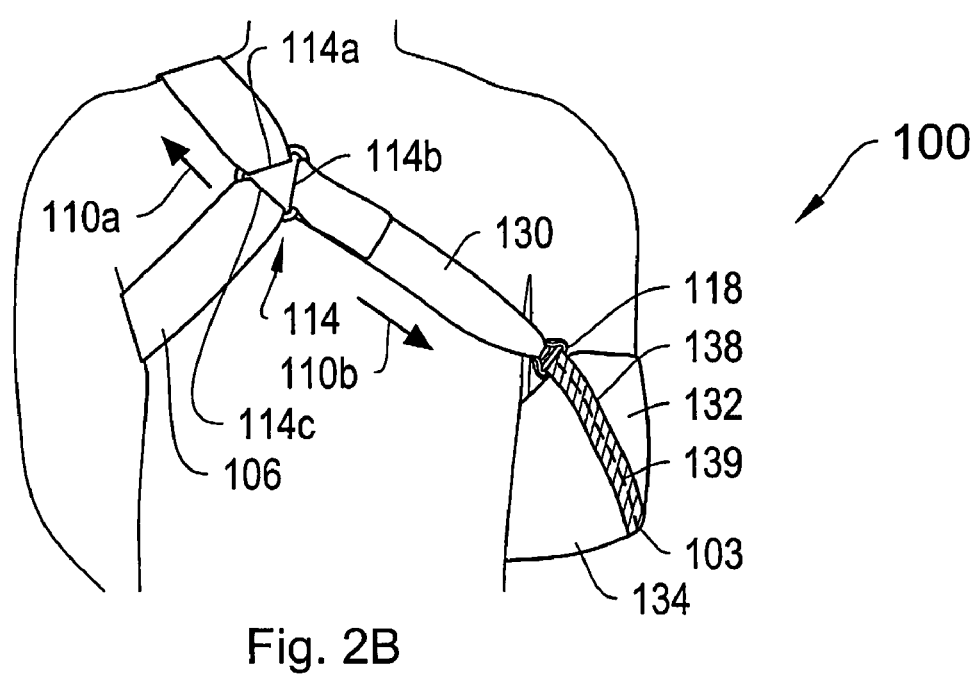

FIGS. 2A and 2B depict a rear view of the sling assembly 100 shown in FIG. 1. As shown in FIG. 2A, the pouch 102 includes a shoulder strap 104 with a rear side 105 that extends over the patient's left shoulder, along the patient's back and attaches to the pouch 102 through triceps D-ring assembly 118, which is located at about the mid-region of the user's triceps 123. The components of an exemplary D-ring assembly 118 are depicted in an exploded view in FIG. 4D. The assembly 118 includes a plastic D-ring 120 and a fabric attachment material 121 that is stitched, glued, or otherwise connected to the D-ring 120 and to the pouch 102. In one implementation the fabric material 121 passes through the D-ring 120, so that two sides of the fabric material 121 can be joined together and attached to the rear of the pouch 102. In one embodiment, this assembly 118 is a fixed connection joining the shoulder strap 104 to the pouch 102. The D-ring assembly 118 and the connection between strap 104 and pouch 102 may optionally be configured to be releasable. For example, the fabric material 121 may be formed with hook and tab materials, similar to materials used for tab 116 (as described below) and may be passed through the D-ring 120 and laid back upon itself so that two sides of the fabric body 121 can be joined together and attached to the rear of the pouch 102 through a Velcro or other hook and tab mating connection. In another example, a clip may be connected to strap 104 and adapted to latch or clip to the D-ring 120 or other appropriate receiving member on the pouch 102.

The rear side 105 of the shoulder strap 104 also attaches to the locking strap 106 in a position along the length of the shoulder strap. In one exemplary configuration, as depicted by the arrows 110a and 110b which are oriented in opposing directions, the locking strap 106 and the shoulder strap 104 are secured by a moveable connection 112 that allows the patient to adjust where the locking strap 106 attaches along the length of the shoulder strap 104. To this end, the moveable connection 112 may include a moveable D-ring assembly that can be moved along the length of the shoulder strap 104 so that it may be positioned at a location that is suited for the size of a particular patient.

Figure 9A:
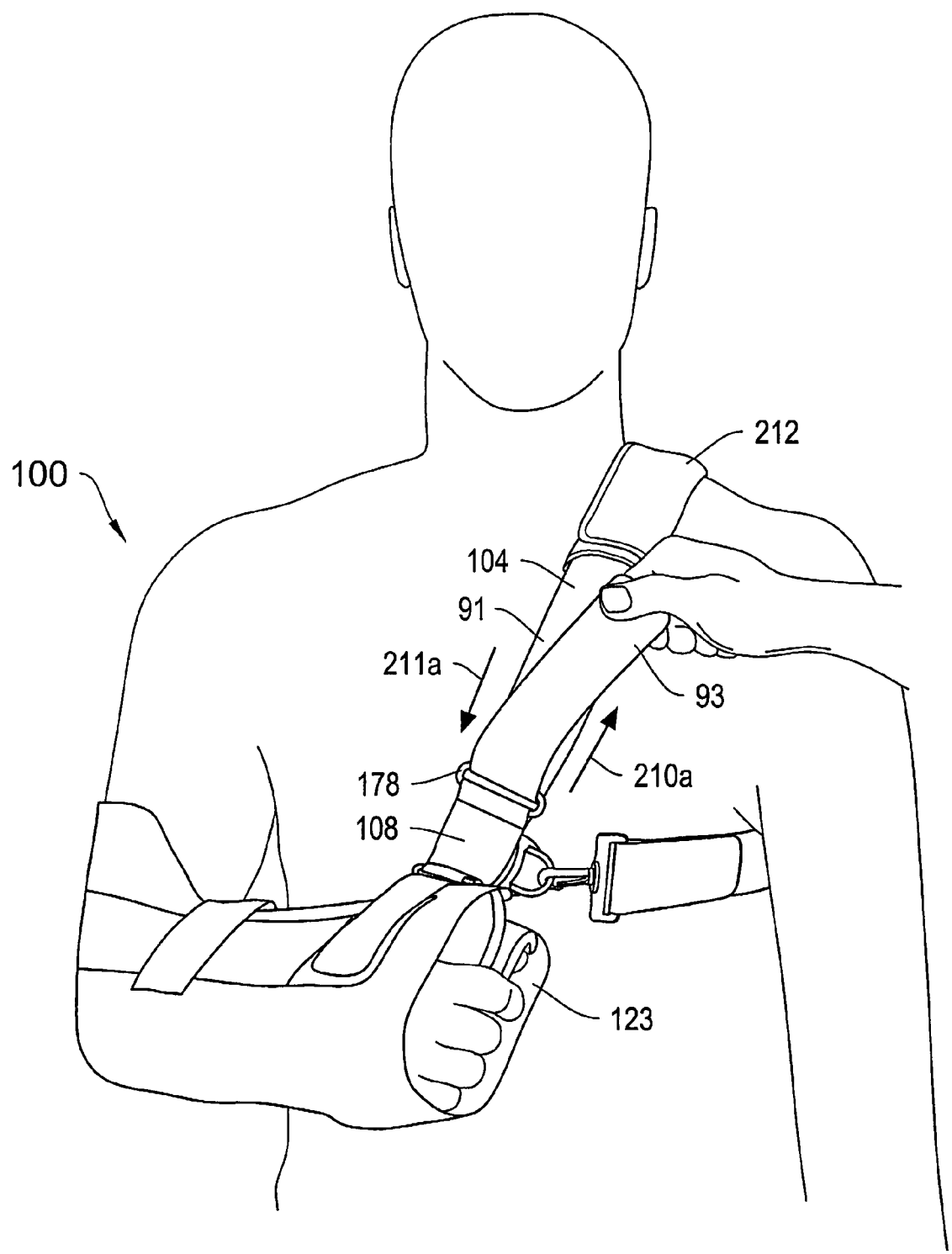
FIGS. 9A-9B depict exemplary mechanisms for adjusting a sling assembly to fit a patient's torso.
Figure 9B:
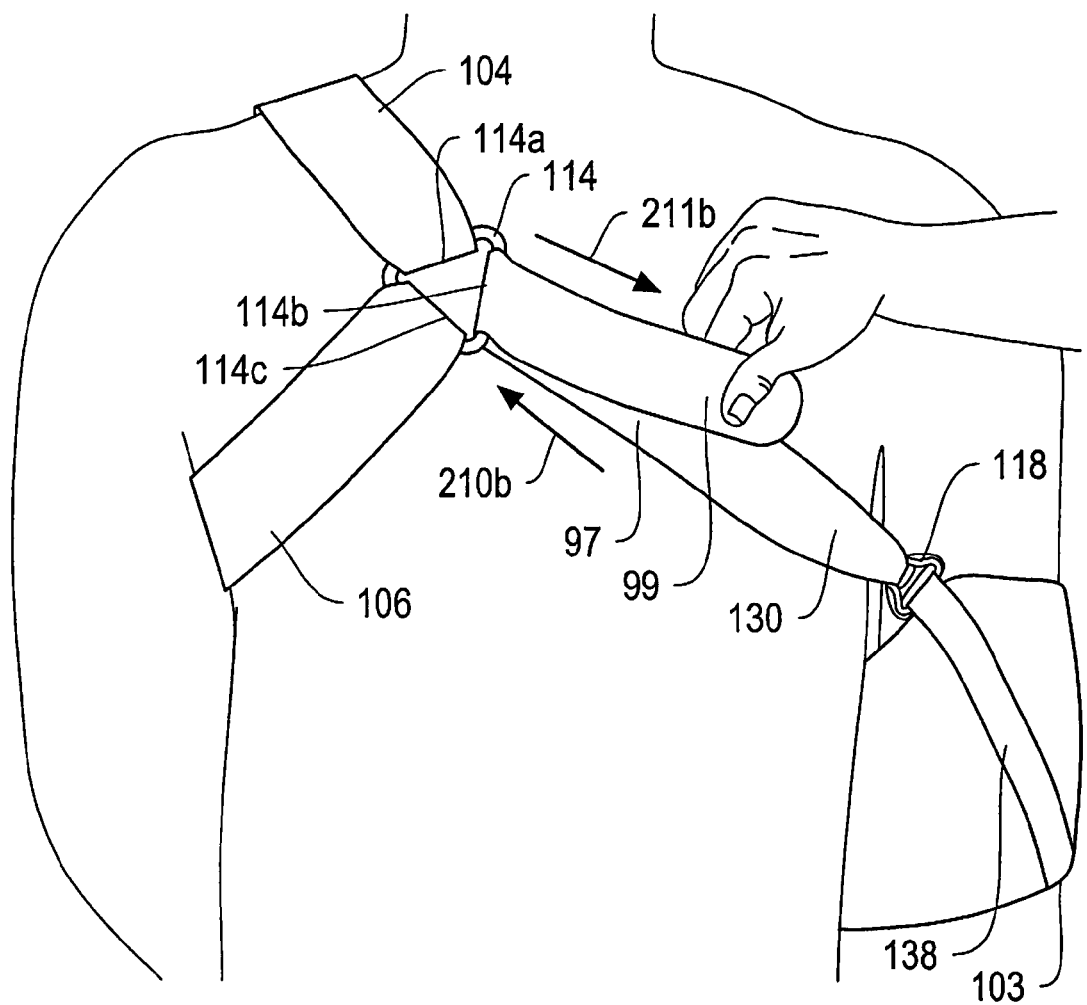

In another exemplary embodiment, the moveable connection 112 is replaced by a buckle or other mechanical fastener. An exemplary fastener is the buckle 114 depicted in FIG. 2B. FIG. 2B depicts the shoulder strap 104 joined with locking strap 106 and a back strap 130 at triangle buckle 114. The triangle buckle 114 is positioned behind the patient (e.g., along the patient's back). One or more of straps 104, 130 and 106 may be adapted to adjustably release, lengthen, shorten and lock about the buckle 114, thereby allowing a user to adjust the length of the applicable strap to achieve desired patient comfort. FIG. 9B depicts in further detail exemplary illustrations of the connection between the locking strap 106, the shoulder strap 104 and back strap 130 for fitting the sling assembly 100 to the user.

Figure 3A:
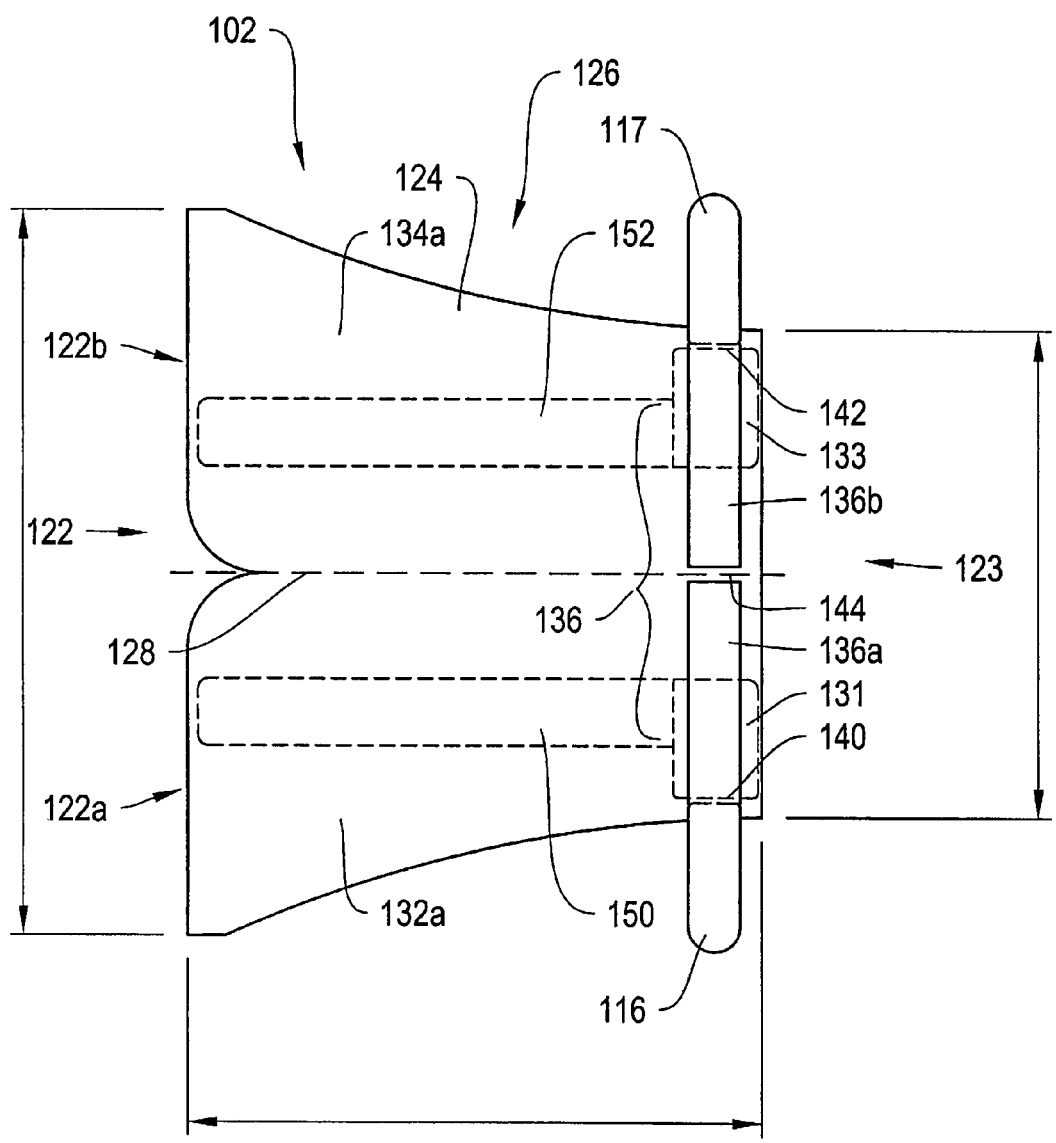
FIGS. 3A-3C depict in more detail the structure of a pouch for a sling assembly.
Figure 3B:
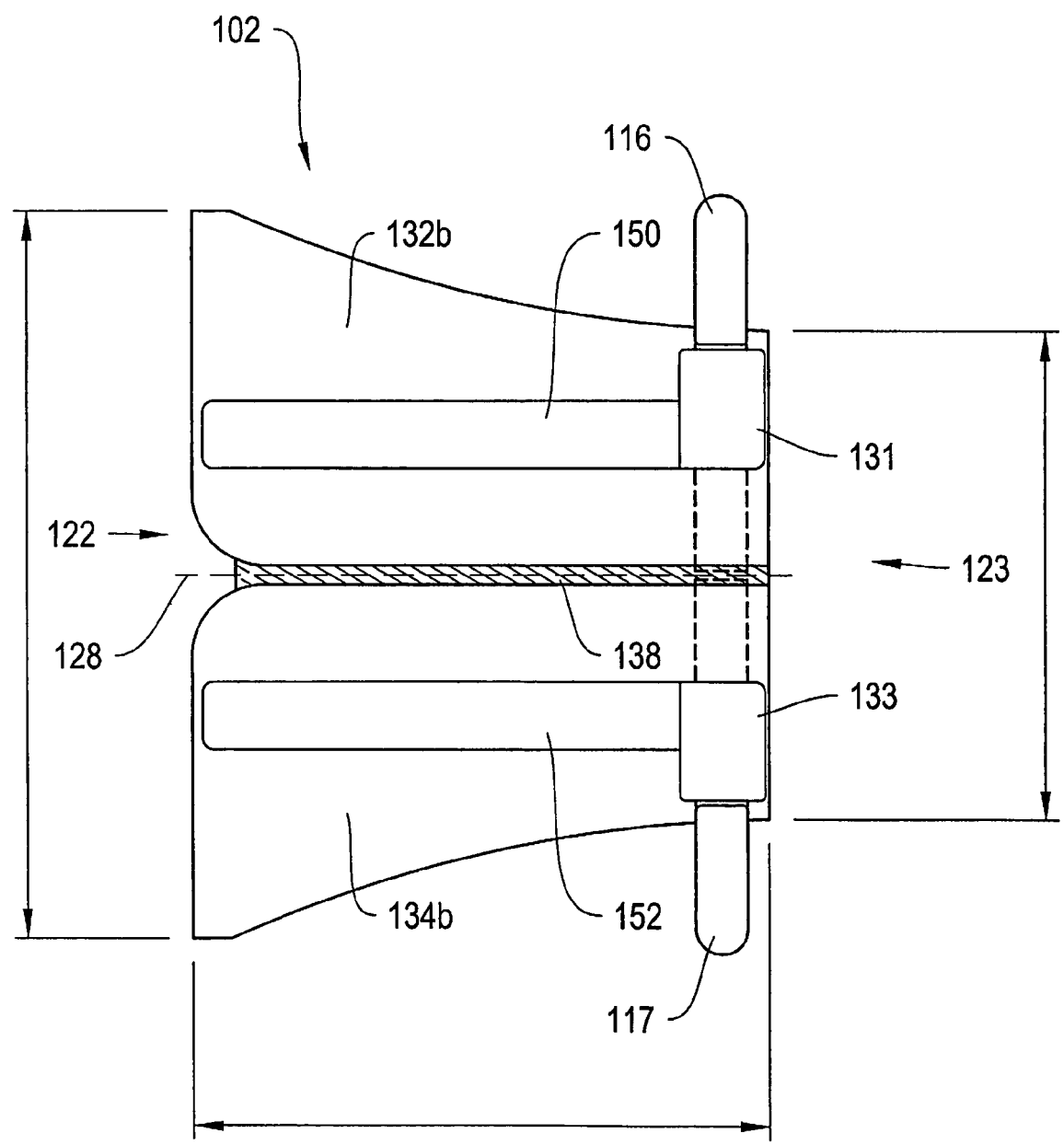
Figure 3C:
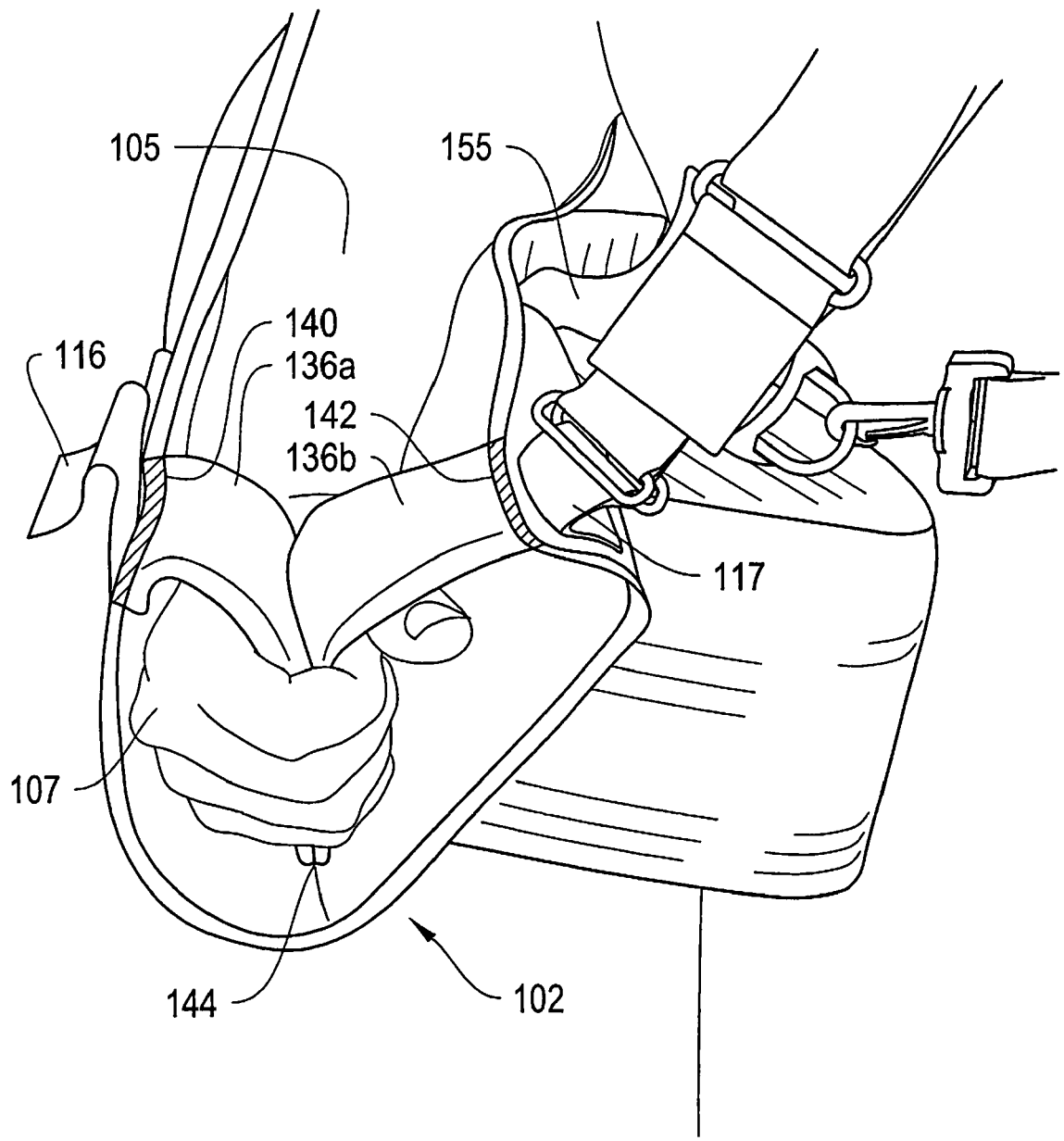

FIGS. 3A-3C depict in more detail an exemplary embodiment of a pouch assembly 102 that may be employed in the sling assembly 100. More particularly, the pouch assembly 102 has a distal portion 123 and a proximal portion 122 and includes a symmetrically-cut sheet of material 124 that is folded along axis 128 and, optionally, stitched or otherwise joined along proximal sections 122a and 122b by seam 139, as shown in FIGS. 2A and 2B. The material 124 for the pouch 102 can be selected from suitable cloth or other material. In certain embodiments the material includes cotton, nylon, canvas or other relatively non-stretchable material. In certain other embodiments, the material includes a stretchable fabric, such as neoprene or other soft polymer. The material may comprise a single layer of material or multiple layers, and optionally may have a coating, such as a coating of a moisture resistant material. The material 124 may also be sized as appropriate to provide a pouch 102 that fits the user's arm 101. The embodiment depicted in FIGS. 3A-3C provides a material 124 having a proximal side 122 of length of about 25 to about 45 inches, with a distal side 122 of a length of approximately 15 inches. Longitudinally, the material 124 extends from elbow to wrist in the depicted embodiment in about 15 to about 25 inches. Any suitable set of dimensions may be selected, and the material 124 prepared and sized accordingly. The seam 139 may be formed through stitching, a Zipper, a Velcro connection, or any other suitable mechanism.

When folded, the pouch 102 will have a front panel 132 and a back panel 134, both of which are shown and laid out flat in FIGS. 3A and 3B, with FIG. 3A depicting the inner faces 132a and 134a of the panels 132 and 134, and FIG. 3B depicting the outer faces 132b and 134b of the panels 132 and 134. As also shown in FIGS. 3A-3C, hook tabs 116 and 117 extend outwardly from the pouch 102 and adjoin the panels 132 and 134 to the shoulder strap 104. More particularly, the tabs 116 and 117 are located on each panel, 132 and 134 respectively, wherein hook tab 116 is stitched or otherwise connected to the inner side 132a of the front panel 132, and hook tab 117 is stitched or otherwise connected to the inner side 134a of the back panel 134 of the pouch 102. As will be shown in more detail in reference to FIGS. 4A-4C, the hook tabs 116 and 117 connect the shoulder strap 104 to the pouch 102 by connecting to respective D-rings on the locking assembly 108. This configuration allows each panel 132 and 134 to be independently released from the locking assembly 108, which is described in further detail below with reference to FIGS. 10A and 10B.

In the depicted embodiment, the hook tabs 116 and 117 are formed of separate pieces of material that are affixed to the panel faces 132a and 134a, respectively. In optional embodiments, the hook tabs 116 and 117 form a single piece of material that extends across and through the distal end 123 of the pouch 102 and is stitched in place along the distal end 123, as desired to secure the single piece of material along the panels 132 and 134.

The pouch 102 may be configured with additional components for further supporting the arm. In one aspect, as shown in FIG. 3B, an inelastic member 138 is provided to reinforce the folded axis 128. With continued reference to FIG. 1, the inelastic member 138 can impede the stretchable material 124 from unduly sagging and pulling the strap 104 downward against the user's shoulder in the vertical direction 146, and thereby assists in relieving pressure on the user's neck. This feature is particularly useful when the material 124 is formed of a stretchable material. In particular, the inelastic member 138 allows the pouch 102 to be made of neoprene or other stretchable elastic material, which allows the pouch 102 to flex and provide flexibility to the user's arm 101 in the lateral and horizontal direction 148, as shown in FIG. 1, but impedes sagging in the vertical direction 146. The inelastic member 138 may include nylon, polyester, or other suitable inelastic material. The inelastic member 138 may be formed of a flexible fabric, such as the fabric typically used in an audible seat belt. In other embodiments the inelastic member 138 may be formed of metal, polymer or other rigid material.

As another exemplary additional feature, as shown in FIGS. 3A and 3C, the pouch 102 may include a hand strap 136 that extends longitudinally across the distal section 123 of the pouch 102. In the depicted embodiment the hand strap 136 has two components 136a and 136b, with component 136a oriented on the inside face 132a of the front panel 132 and the other 136b on the inside face 134a of the back panel 134. The hand strap 136 restricts the movement and sliding of the pouch 102 back toward the elbow 103. This helps keep the wrist 105 and hand 107 supported, and also improves patient comfort. In the embodiment depicted in FIGS. 3A and 3B each hand strap 136 is sewn directly to the pouch at seems 140 and 142, respectively, thereby providing a strap that the patient can slip between their thumb and their fingers, particularly between the thumb and forefinger. Moreover, both components 136a and 136b are sewn to the pouch 102 along the folded access 128 at seam 144, as further shown in FIG. 3C. In one embodiment, the hand strap 136 may be formed of any suitable cloth or other material, for example a nylon backing strip having a hook and loop fastener material formed thereon.

As another exemplary feature shown in FIGS. 3A and 3B, the pouch assembly 102 includes the joining strips 150 and 152 that extend laterally across the outside surfaces 132 and 134 respectively, of the pouch 102 and are configured to receive the tabs 116 and 117. The pouch 102 also includes a cross-strap 150 described above with reference to FIG. 1 and a support pad described below with reference to FIGS. 10A-

10B. FIG. 3A shows the joining strips 150 and 152 as dashed lines to indicate that they are on the reverse side of the pouch 102.

Figure 4A:
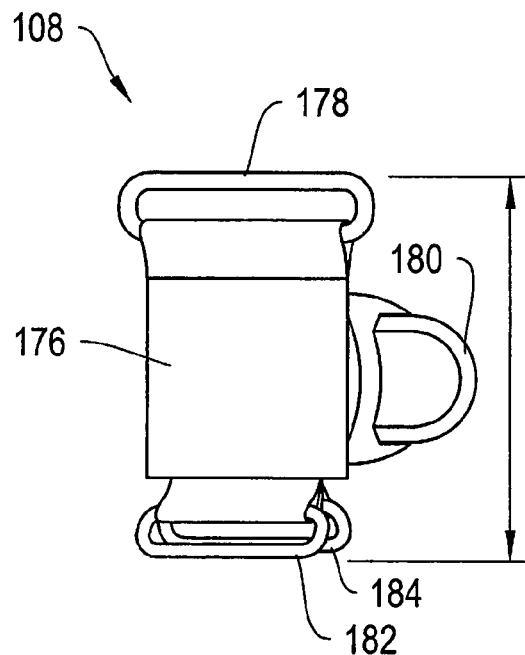
FIGS. 4A-4D depicts in more detail the structure of exemplary attachment buckles for use with a sling assembly according to an illustrative embodiment of the invention.
Figure 4B:
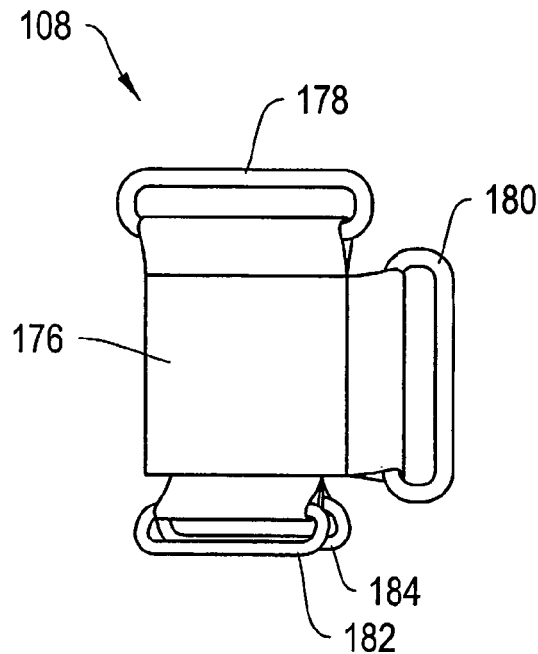
Figure 4D:
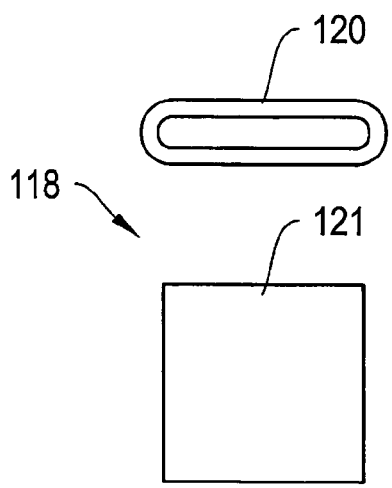
Figure 4C:
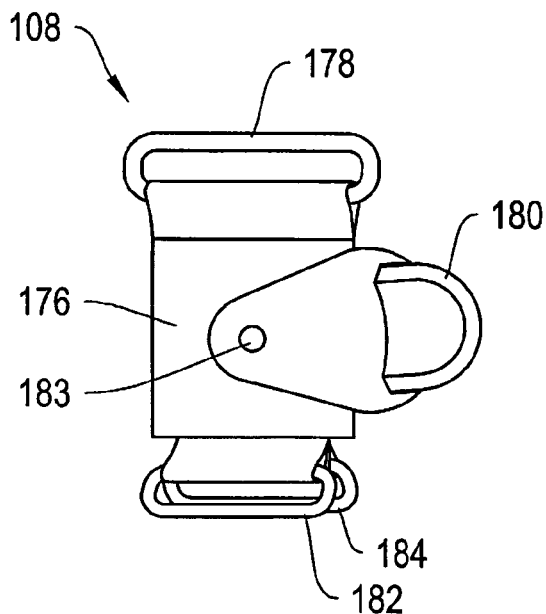

FIGS. 4A-4D depict in more detail various exemplary embodiments of buckles that may be used with the sling assembly 100. FIGS. 4A-4C depict exemplary embodiments of the locking assembly 108 that is shown in FIG. 1. FIG. 4D depicts the locking assembly 118 describe above. With reference to FIGS. 4A-4C, the locking assembly 108 includes a central body 176 fastened to a shoulder strap D-ring 178, a locking strap D-ring 180, a D-ring 182 for the hook tab 116 on the front panel 132 of the pouch 102, and a D-ring 184 for the hook tab 117 of the rear panel 134. The central body 176 may be attached to the foregoing rings by stitching, glue, Velcro, Zipper, or other mechanical fasteners. For example, as shown in FIG. 4C, the locking strap D-Ring 180 may optionally be swivel mounted to the body 176 through a rivet 183, a snap or other suitable reversible mechanical connector. This can help the strap lie flat against the patient's body. Any one or more of the rings may be accordingly swivel mounted to the member 176.

Figure 8:
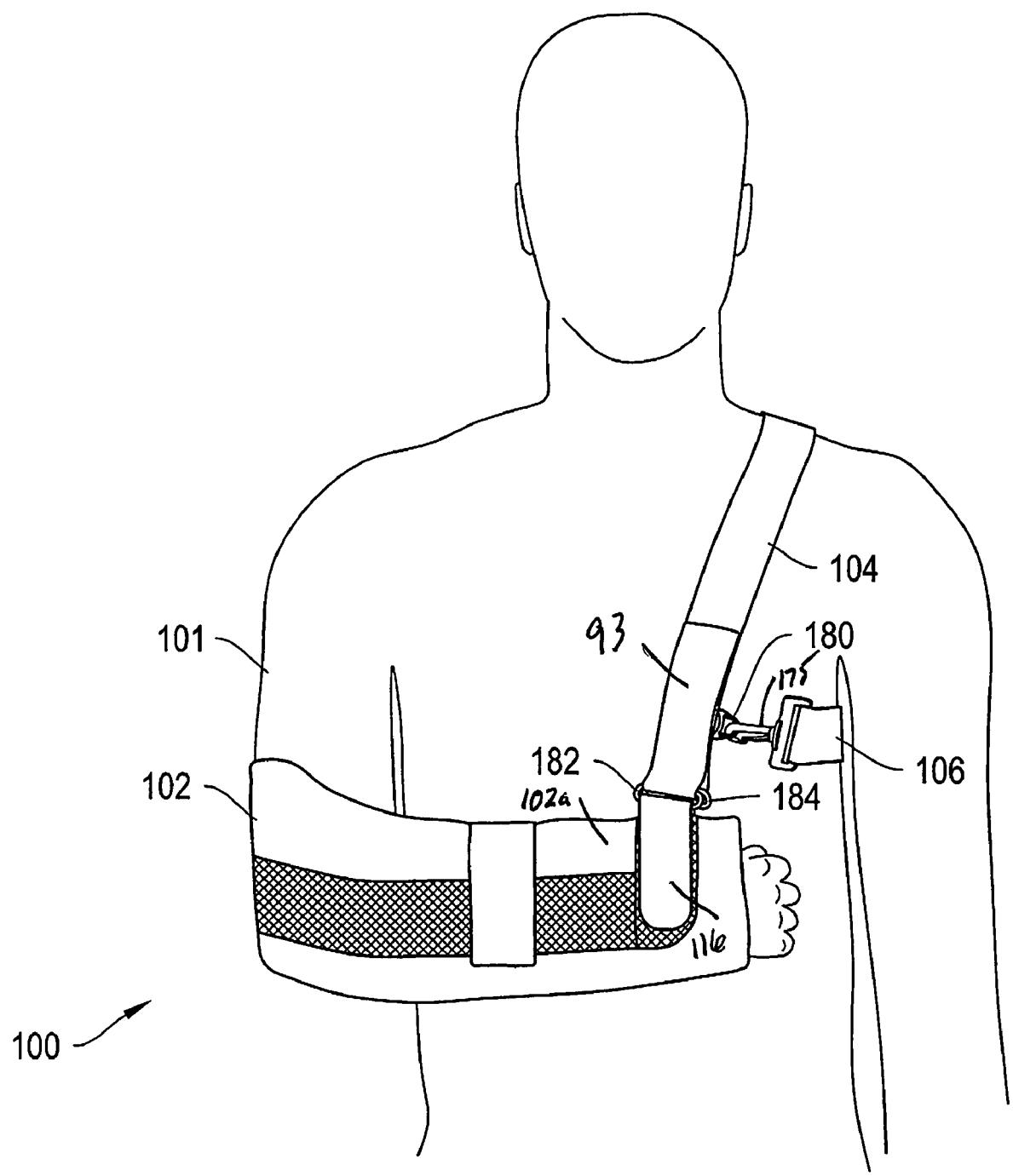
FIG. 8 depicts an alternative exemplary locking assembly that may be used to connect the pouch to one or more straps.

In operation, the locking assembly 108 is positioned proximate to the upper distal portion of the pouch 102a (as shown in FIGS. 7 and 8) and oriented so that D-rings 182 and 184 receive hook tabs 116 and 117 from the sling 100 to adjoin the pouch 102 to the locking assembly 108. In particular, the hook tabs 116 and 117 are inserted through the underside of the D-rings, 182 and 184 respectively, and are pulled back upon the pouch 102 and mated with hook and loop fastener materials 131 and 133, respectively. The hooked tabs 116 and 117 are adapted to contain appropriate hook and loop, Velcro or other receiving materials for allowing the faces 116 and 117 to affix to the surfaces 131 and 133. The connections formed between component 116 and the hook and loop fastener 131 and between face 117 and hook and loop fastener 133 are releasably adjustable and positionable by the user. In this respect, the user can pull the tab 116 through the D-ring 182 on the locking assembly 108 until the tab 116 is a desired length and thereafter apply the tab 116 to the surface 131. This surface connection between tab 116 and connecting face 131, and the connection between tab 117 and face 133, can be released by the user to allow the front flap 132 or the back flap 134, as desired, to be removed or turned downwardly, as described more fully below in reference to FIGS. 10A-10B.

Figure 5A:
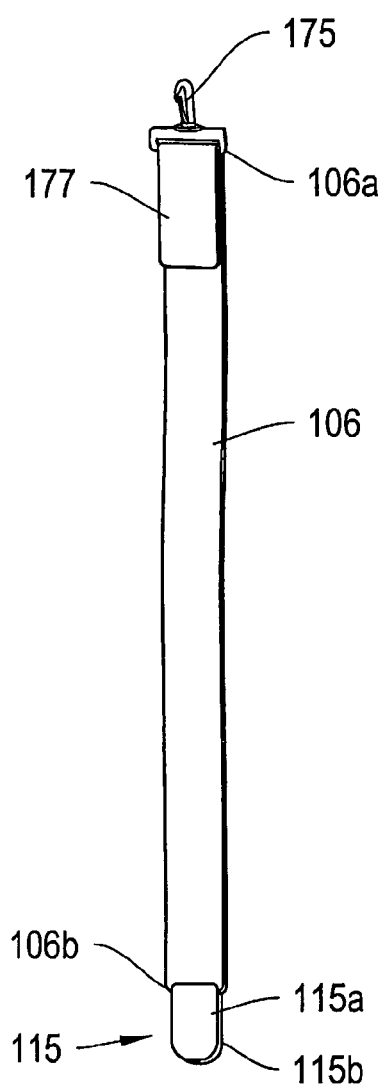
FIGS. 5A-5B depict exemplary locking straps that may be used with a sling assembly, according to an illustrative embodiment of the invention.
Figure 5B:
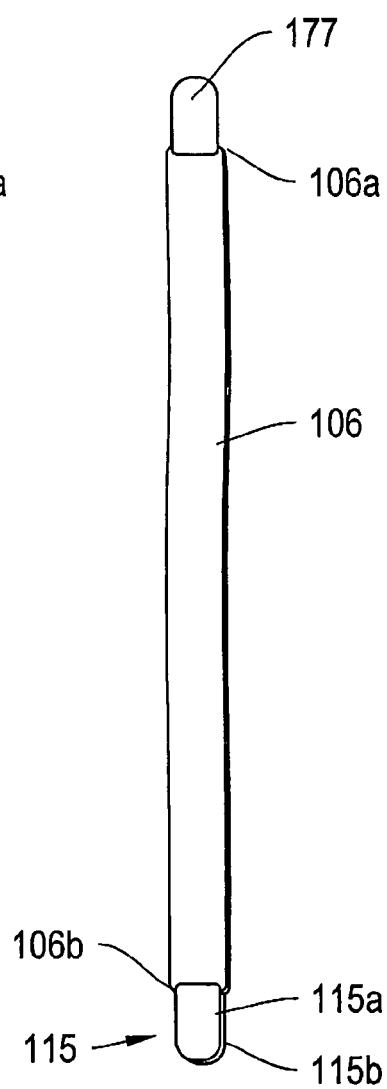

FIGS. 5A-5B depict exemplary embodiments of the locking strap 106 and exemplary latches and clasps for connecting the strap 106 to the shoulder strap 104 and to the locking assembly 108. In certain embodiments, such as the sling assembly 100 of FIG. 1, the locking strap 106 joins the locking assembly 108 and the shoulder strap 104, thereby locking the shoulder strap 104 into place and preventing or reducing the tendency of the shoulder strap 104 to travel towards the patient's neck, where it can cause discomfort and irritation. More particularly, as shown in FIG. 5A, the strap 106 has a first end 106a connected to a latch 175 through the tab 177. Tab 177 includes a Velcro, hook and loop or other fastening surface that allows tab 177 to loop through the ring of 175 and lay back upon the upper end 106a of the strap 106, securing latch 175. Latch 175 is thereby oriented to connect to the locking assembly 108 at the D-ring 180. The latch 175 allows the user to release and reattach the first end 106a of the locking strap 106 to and from the locking assembly without adjusting the length of the strap 106. Any suitable mechanical fastener may be used in lieu of latch 175. For example, as shown in FIG. 5B, the strap end 106a may be configured so that tab 177 mates directly with the top surface of the shoulder strap 104 (or an intermediate locking assembly surface). Preferably, the fastener is releasable to allow the user to remove and reattach the strap 106 to and from the locking assembly 108, the shoulder strap 104 or the pouch 102. Other exemplary attachment mechanisms for locking strap 106 are described below with reference to FIGS. 7 and 8.

As shown in FIGS. 5A and 5B, the second end 106b of the locking strap 106 has a clasp 115 for joining the strap 106 to the reverse side 105 of the shoulder strap 104, as depicted in FIG. 2A. More particularly, the clasp 115 has two tabs 115a and 115b, wherein tab 115a has an under side that includes a Velcro, hook and loop or other mechanical mating surface and that attaches to the top side of the shoulder strap 104, while tab 115b has a topside mating surface that attaches to the underside (not shown) of the shoulder strap 104 along the hind side 105 of the patient. In this embodiment, the attachments between tabs 115a/115b and the strap 104 are made through Velcro attachment layers on the applicable sides of strap 104. In one configuration, the clasp 115 is dimensioned so that is attaches across the full width of the shoulder strap 104.

In an alternative embodiment, the second end 106b of the strap 106 is configured with a Velcro, hook and loop or other feature to join to the buckle 114, as depicted in FIG. 2B. The second end 106b is looped through the buckle 114 and affixed back on itself through a Velcro or other releasable attachment, or optionally stitched or otherwise permanently affixed to the buckle 114. Any suitable clasp, clip or other mechanical fastener may be used to attach the strap 106 to the reverse side 105 of the strap 104.

Figure 6:
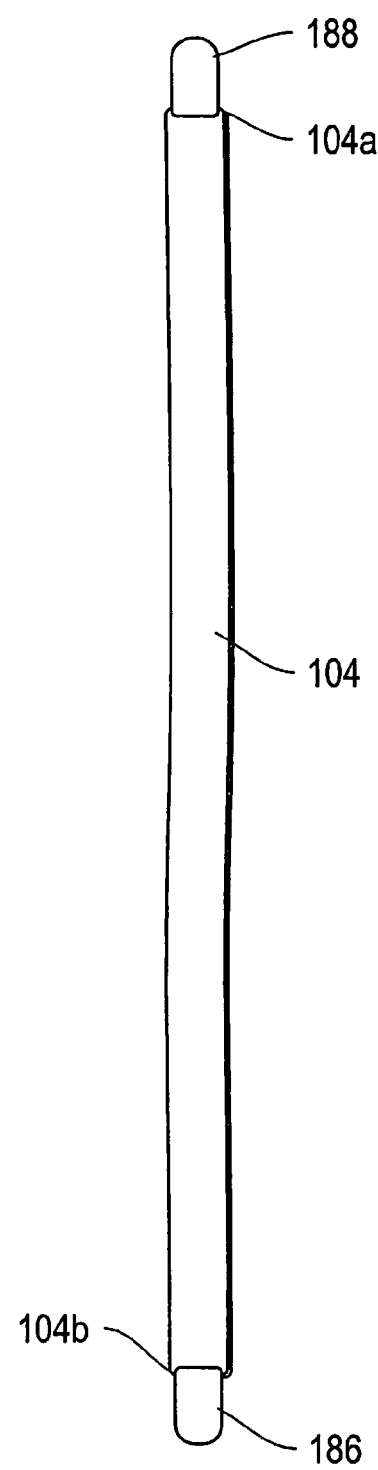
FIG. 6 depicts an exemplary shoulder strap that may be used with a sling assembly, according to an illustrative embodiment of the invention.

FIG. 6 depicts an exemplary embodiment of the shoulder strap 104 in more detail. In particular, FIG. 6 shows the shoulder strap 104 as a length of material that has a tab of hook and loop fastener 186 and 188 at each end 104a and 104b. In the depicted embodiment, the shoulder strap 104 joins to the locking assembly 108 by inserting tab 188 through the D-ring 178, and pulling the tab 188 back upon the end 104a of the shoulder strap 104 where it is mated with hook and loop fasteners on the end 104a. The hooked tab 188 is adapted to contain appropriate hook and loop, Velcro or other receiving materials for allowing it to affix to surface 104a. The connection between tab 188 and the end 104a of the strap 104 can be released and adjusted by the user, as explained in further detail below with reference to FIG. 9A. The strap 104 also has a fastener 188 on its end 104b which connects the strap 104 to the locking strap 106 through a connector assembly, such as assembly 112 or triangle buckle 114, as described above. The strap 104 may be made of nylon, neoprene, cotton, canvas, or any suitable material or group of materials. It may comprise a single layer of material or multiple layers, and optionally may have a coating, such as a coating of a moisture resistant material. As shown more clearly in FIGS. 7A and 9C, the shoulder strap may also be provided with a pad 212 for fitting along the patient's shoulder to provide patient comfort. Moreover, the strap 104 depicted in FIG. 6 may also be adapted and used with back strap 130, as shown in the embodiment of FIG. 2B.

The exemplary embodiments described above illustrate a locking assembly 108 which includes a 4-point-of-attachment buckle as an intermediate member that used to connect the pouch 102 to the shoulder strap 104 and the locking strap 106. FIGS. 7 and 8 depict other exemplary embodiments of a sling assembly 100 that have alternative locking assemblies. In contrast to the buckle assemblies of FIGS. 4A-4C (as used in the sling assembly 100 of FIG. 1), the rings 182, 184 and 180 of the locking assembly of FIGS. 7 and 8 are not joined by an intermediate member 176 and do not include an upper ring 178. Instead, the rings are dispersed about one or more of the pouch 102 and the shoulder strap 106. In the exemplary embodiment of FIG. 7, the ring 180 is fixed directly to the upper distal end 102a of the pouch 102 by stitching, zipper, or other mechanical fastener such that it is positioned to receive the latch 175 from the locking strap 106. In the exemplary embodiment of FIG. 8, the ring 180 is fixed directly to the shoulder strap 104 by stitching, zipper, or other mechanical fastener and positioned to receive the latch 175 from the locking strap 106. In both examples, the rings 182 and 184 are positioned to receive tabs 116 and 117 (not shown) as described above but are configured to join directly to the strap 104, rather than indirectly through the use of intermediate loop 178, as described above with reference to FIGS. 4A-4C. In the depicted embodiments, the strap 104 has an end 93 that may optionally be configured with a separate tab 188 (not shown) and is looped through both of the rings 184 and 182 from their torso side to the outside and laid back upon the strap 104 in a Velcro, hook and loop or other mechanical connection.

In one aspect, the locking assembly 108 and the shoulder 104 and locking 106 straps, and the back strap 130 when applied, are releasably connected to allow the user to adjust the positioning of the sling assembly 100 to comfortably fit the user's torso. FIGS. 9A and 9B depict an exemplary fitting technique using the locking assembly 108 and the triangle buckle 114. FIG. 9A more particularly illustrates the use of the locking assembly 108 to adjust the fitting of the sling 100. As described above, the shoulder strap 104 has a bottom portion 91 and a top portion 93 that slides through the ring 178 on the locking assembly 108 and lays back upon bottom portion 91 in a Velcro, hook and loop or other reversible connection. To adjust the length of the strap 104, and hence to tighten or loosen the fit of the sling 100, the user first disengages the top portion 93 from the bottom portion 91. The user can then tighten the sling 100 by pulling the portion 93 through the ring 178 in the direction of arrow 210a, thereby pulling portion 91 in the direction of arrow 211a to tighten the strap 104a. To loosen the fit of the sling 100, the user pulls portion 91 away from the ring 178 in the direction of arrow 210a and feeds portion 93 through the ring 178 in the direction of arrow 211 a to loosen the strap 104a.

FIG. 9B more particularly depicts the use of the triangle buckle 114 to adjust the fitting of the sling 100. As shown, the back strap 130 is adapted to loop under the side 114b of the buckle 114 and lay back upon itself in a releasably attaching fashion, while strap 104 and strap 106 are stitched to their respective sides of the triangle buckle 114 (side 114a and 114c respectively). More particularly, the back strap 130 has a bottom portion 97 and a top portion 99 that slides through side 114b of the buckle 114 and lays back upon bottom portion 97 in a Velcro, hook and loop or other reversible connection similar to the connection between top portion 93 and bottom portion 91 of strap 130 described above. To adjust the fit of the sling 100, the user adjusts the length of the back strap 130. To do this, the user lifts the upper portion 99 of the strap 130 to disengage portion 99 from the lower portion 97 of strap 104b. Once the portions 99 and 97 are disengaged, the strap 130 can be lengthened by pulling the portion 97 in the direction of arrow 211b toward the user's elbow, thereby loosening the connection of strap 130 and extending the length thereof to provide a looser fit for the sling 100. The upper portion 99 is then laid along and adjoined to the lower portion 97 to secure the strap 130 in the selected position by using Velcro, hook and loop or any other suitable fastening mechanism. To tighten the fit of the sling 100, the user disengages portion 99 from portion 97 and pulls portion 99 in the direction of arrow 211b, thereby pulling end 97 in the direction of arrow 210b to tighten the strap 104. This adjusts the positioning of buckle 114 toward the user's lower right side along direction path line 211b. The upper portion 99 is then laid along and adjoined to the lower portion 97 to secure the strap 104 in the selected position by using Velcro, hook and loop or any other suitable fastening mechanism.

The fitting mechanisms described in FIGS. 9A and 9B exemplify the adjustability of the shoulder strap 104 and its use in adjusting the fitting of the sling assembly 100. An analogous configuration can be adapted for the locking strap 106, wherein one or both ends 106a and 106b can include a Velcro, hook and loop or other mechanical fastening mechanism and can adjustably connect to the locking assembly 108 and/or the buckle 114 in a similar manner as the strap 104.

Figure 10A:
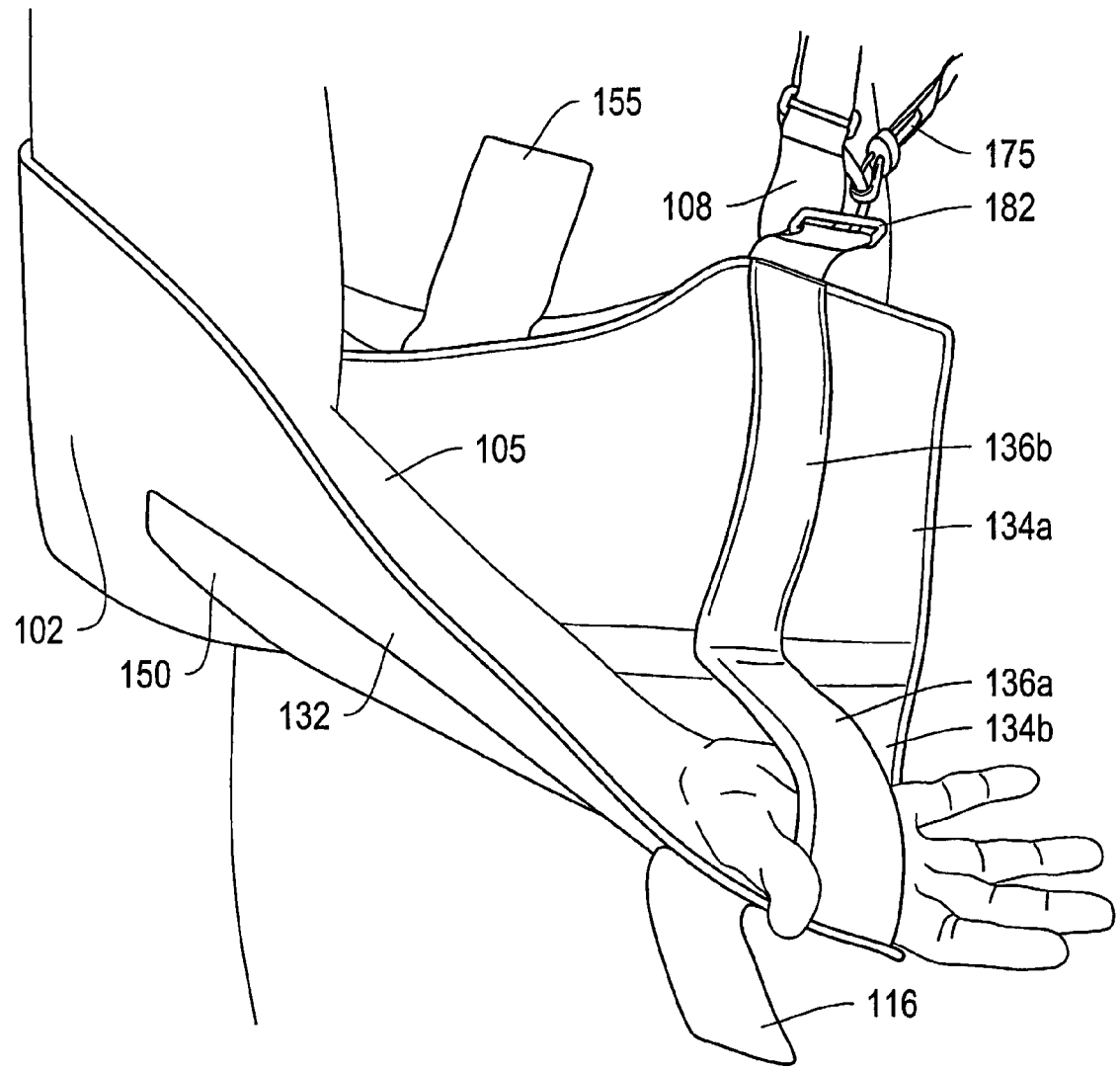
FIG. 10A depicts a sling assembly with an outer pouch flap opened away from the patient for allowing the patient to perform exercises to rehabilitate an injured arm.
Figure 10B:
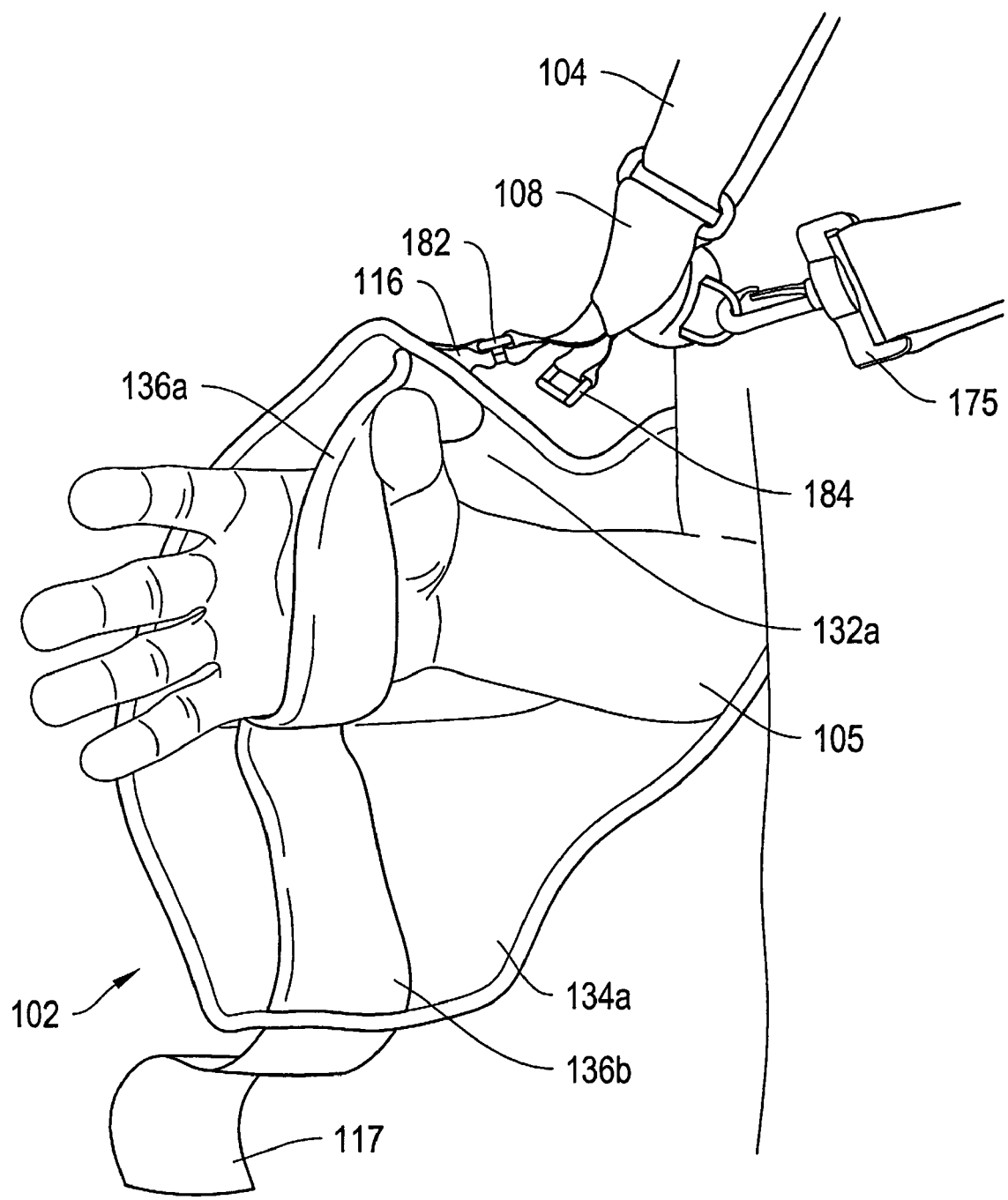
FIG. 10B depicts a sling assembly with an inner pouch flap opened into the patient's torso for allowing the patient to perform exercises to rehabilitate an injured arm.

In another aspect, the flaps 132 and 134, the straps 104 and 106 and the locking assembly 108 are reversibly and adjustably interconnected to allow a physician to access the patient's arm without removing the sling 100 from the patient and without altering the length of the locking strap 106 or other straps. FIGS. 10A-10B depict the arm sling 100 fitted to a patient and being partially opened so that the patient's arm has some degree of movement and the patient can perform rehabilitation exercises. As described above, the patient may release the hook-tab 116 and/or 117 from its respective D-ring, 182 and 184, thereby disconnecting the front panel 132 or back panel 134 from the locking assembly 108. This allows the patient to release the arm from the sling 100, without having to remove the sling 100 or disconnect other clasps or connectors, such as the shoulder strap connector 178, which would then have to be reconnected and adjusted when later worn by the client.

By releasing one or both panels of the pouch 102, the arm is provided with a certain range of motion for performing rehabilitation exercises without disengaging any other connection on the sling assembly 100 or requiring readjustment of shoulder strap 104 or locking strap 106. More particularly, FIG. 10A depicts the tab 116 released from the buckle loop 182, and the front flap 132 released and opened away from the patient's torso, allowing the patient to remove the arm from the pouch 102 for performing rehabilitation or other purposes but retaining the connection between the back panel 134 and the locking assembly 108 (and, hence, the connection between the back panel 134 and the shoulder strap 104). FIG. 10B depicts the tab 117 released from the buckle loop 184 of assembly 108, and the back flap 134 of the pouch 102 turned down and toward the patient's torso, allowing the patient to remove the arm from the pouch for performing rehabilitation or other purposes but retaining the connection between the front panel 132 and the locking assembly 108 (and, hence, the connection between the front panel 132 and the shoulder strap 104).

Figure 11A:
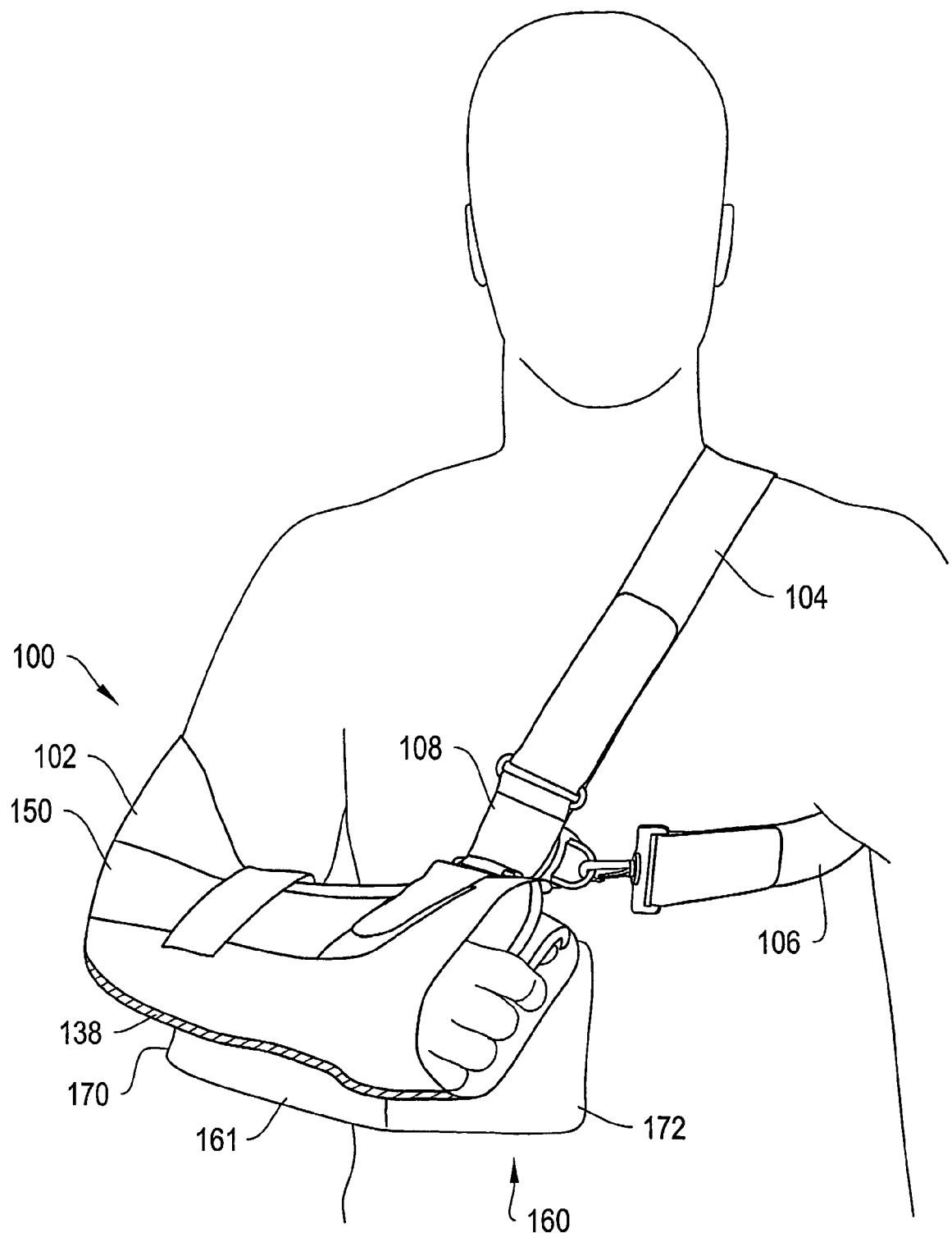
FIGS. 11A-11C depict an abduction pillow for use with a sling assembly to provide ergonomic support for a patient's arm.
Figure 11B:
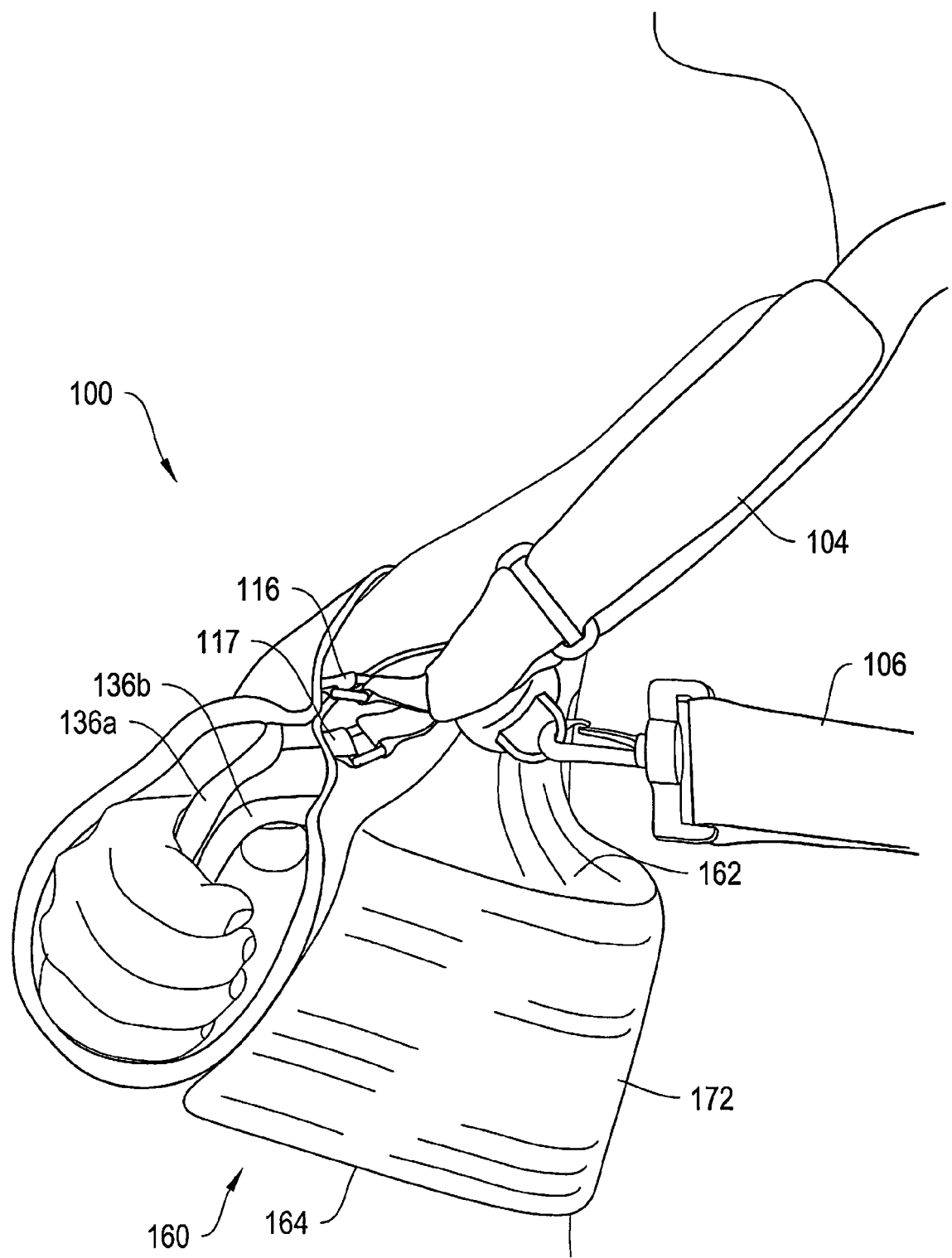
Figure 11C:
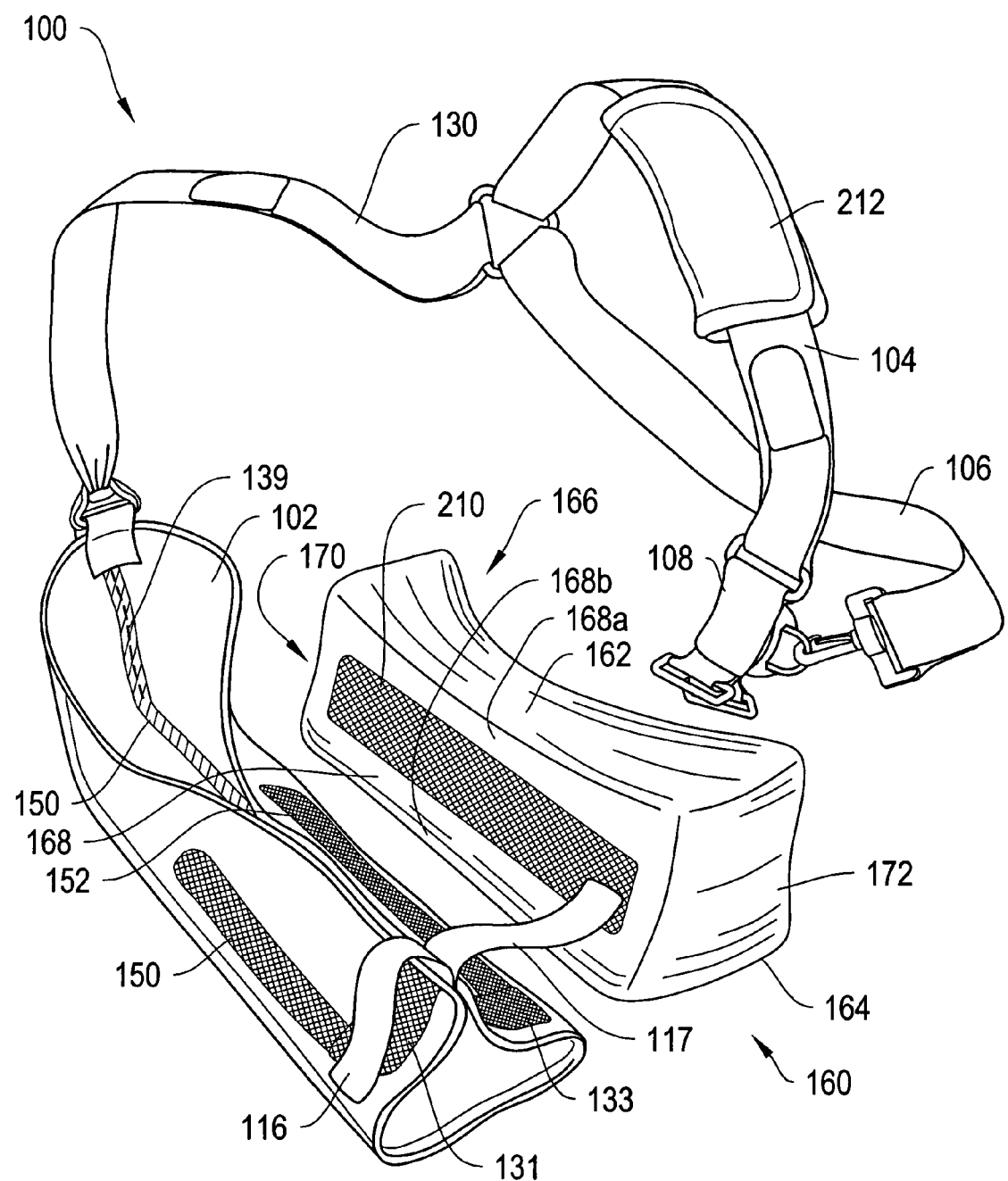

In another aspect, as noted above, the sling assembly 100 may be combined with an abduction pillow or other suitable support pad to further support the user's arm. FIGS. 11A-11C depict the sling assembly 100 in combination with a pad 160. As shown more particularly in FIGS. 11A and 11B, the pad 160 is an abduction pillow that includes a cushion 161 having top side 162, bottom side 164, proximal end 170 and distal end 172, along with an interior surface 166 contoured to fit next to the user's torso and an exterior surface 168 adapted to extend away from the user's torso and receive the pouch 102. Any suitable cushion or pillow may be used.

The abduction pillow 160 may be shaped to accommodate the anatomy of the wearer's forearm and hand and to conform to the patient's abdomen. The pillow 160 may also be configured to provide ergonomic support for the user's limb. As shown in FIGS. 11B and 11C, the bottom side 164 of the pad 160 is wider than the top side of 162, as measured in a direction extending from the user's torso toward the pouch 102, such that the upper edge 168a of surface 168 is closer to the torso than is the bottom edge 168b, which extends surface 168 away from the torso to ergonomically support the arm 101 when the arm 101 is positioned within the sling 100. In one exemplary configuration, the proximal end 170 and distal end 172 of the pad 160 are of approximately equal width, as measured in a direction extending from the user's torso toward the pouch 102. In such a configuration, the pad 160 pushes the user's arm away from the torso, forming an angle between the upper arm and the torso, without causing flexion of the forearm about the elbow.

As shown in FIG. 11C, the abduction pillow 160 also includes an attachment strip 210, such as Velcro, Zipper or other hook and loop connector, that is affixed to the exterior surface 168 for connecting to the joining strip 152 of the sling assembly 100. By connecting the pillow 160 to the joining strip 152, the pillow 160 is stabilized against the user's abdomen for further supporting the arm. The abduction pillow 160 and sling 100 may be used by a patient in conjunction with post-operative rehabilitative care provided to the patient by an orthopedic surgeon, sports medicine professional, or other health care provider. Intended to provide immobilization and abduction to treat a wide range of conditions affecting the pectoral girdle, the shoulder abduction sling described herein is well suited for use as a part of a postoperative or post-injury rehabilitation program for arthroscopic procedures, rotator cuff tears, thermal capsulorrhapy or other procedures to treat capsular shifts or tears, subluxations, dislocations, and other shoulder instabilities.

The overall design of the arm sling 100 permits the sling to be put on with minimal or no assistance from another person. The Velcro, hook and loop and other suitable fasteners are easy to secure together with one hand, and the shoulder strap 104 and the locking strap 106 are positioned to facilitate donning of the sling. The sling assembly 100 is also configured so that it can be used interchangeably on the right arm or the left arm. In one configuration, when the sling of FIGS. 11A-11C is placed on the user's left arm, the sling assembly is positioned so that panel 132 is aligned next to the user's torso (becoming the back panel) and panel 134 is aligned on the external side of the user's forearm (becoming the front panel), and the attachment strip 210 on the abduction pillow 160 joins with the joining strip 150. It is also foreseen that the restraining straps could be secured to the pouch or the locking assemblies and components by a wide variety of fastening means including pinning, hook and loop type fasteners, snaps, clips, adhesives, threading through slits, slots or openings or other means.

It is to be understood that while certain forms of the present invention have been illustrated and described herein, it is not to be limited to the specific forms or arrangement of parts described and shown. Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

The invention claimed is:

1. A sling for supporting an arm comprising
a pouch for receiving a user's arm and having a distal portion near the region of the user's wrist, a proximal portion near the region of the user's elbow, a front panel and a back panel,
a shoulder strap having a front portion and a rear portion,
a locking strap having a front portion and a rear portion that extends under the user's arm and connects with the shoulder strap at a position along the user's back, and
a locking assembly comprising
a first connection point attached to the distal portion of the pouch for connecting the shoulder strap to the pouch, and
a second connection point positioned along the front portion of the shoulder strap to be disposed between the first connection point and the user's shoulder for connecting the front portion of the locking strap to the shoulder strap.

2. The sling of claim 1, wherein the locking assembly attaches to the front panel of the pouch through a first tab on the front panel.

3. The sling of claim 2, wherein the first tab is disengagable and re-attachable from the locking assembly so as to allow the front panel to open away from the user's torso without disengaging the back panel from the locking assembly.

4. The sling of claim 1, wherein the locking assembly attaches to the back panel of the pouch through a second tab on the back panel.

5. The sling of claim 4, wherein the second tab is disengagable and re-attachable from the locking assembly so as to allow the back panel to open into the user's torso without disengaging the front panel from the shoulder strap.

6. The sling of claim 1, wherein the locking assembly includes a four-point of attachment buckle.

7. The sling of claim 1, wherein the locking strap movably attaches to the shoulder strap at the locking assembly.

8. The sling of claim 7, wherein the locking strap includes a latch adapted to releasably connect to the locking assembly without altering the length of the locking strap.

9. The sling of claim 1 comprising a support pad having a first surface for resting against the user's torso, a second surface facing away from the user's torso and for supporting the pouch, a top surface, and a bottom surface, and being configured so that the second surface angles away from the user's torso.

10. The sling of claim 9, wherein the bottom surface of the support pad is wider than the top surface of the support pad.

11. The sling of claim 9, wherein the support pad has distal and proximal sides of equal width.

12. The sling of claim 9, wherein the support pad includes a stabilizing strap attached to the second surface of the support pad and configured to extend across the pouch and attach to the front panel.

13. The sling of claim 1, wherein the shoulder strap has an adjustable length.

14. The sling of claim 1, wherein the locking strap has an adjustable length.

15. The sling of claim 1, wherein the shoulder strap is configured for positioning on a shoulder opposite of the arm being supported.

16. The sling of claim 1, wherein the pouch includes elastic material on at least one panel.

17. The sling of claim 1, wherein the pouch includes an inelastic spine member positioned along a bottom region.

18. The sling of claim 1 comprising a first hand strap attached to an interior face of a panel on the distal end of the pouch and is positioned to fit between a patient's thumb and forefinger when the sling is applied to the arm.

19. The sling of claim 1 comprising a first hand strap attached to the interior face of the front panel and a second hand strap attached to the interior face of the back panel.

20. The sling of claim 1, wherein the shoulder strap includes a first strap and a back strap adjoined through a rear buckle positionable along the user's back.

21. The sling of claim 20, wherein the rear portion of the locking strap attaches to the shoulder strap through the rear buckle.

22. The sling of claim 1, wherein the sling is interchangeably applicable to a right arm and a left arm.

23. The sling of claim 1, wherein the locking assembly includes a central body positioned to receive the shoulder strap and span between the first and the second connection points.

24. The sling of claim 23 comprising a third connection point positioned along the central body between the first connection point and the shoulder strap.

25. The sling of claim 24, wherein the third connection point comprises a plurality of rings.

26. The sling of claim 23, wherein the second connection point joins the locking strap to the central body.

27. The sling of claim 23, wherein the central body is a unitary piece of fabric.

28. The sling of claim 23, wherein the central body includes one or more loops for receiving a connection point.

29. The sling of claim 23, wherein the second connection point is positioned along the central body between the first connection point and the third connection point.

30. The sling of claim 23, wherein the second connection point is swivel mounted to the central body through a reversible mechanical connector.

31. The sling of claim 30, wherein the reversible mechanical connector is a rivet.

32. The sling of claim 1, wherein the second connection point joins the locking strap directly to the shoulder strap.

33. The sling of claim 1, wherein at least one connection point is a ring.

34. The sling of claim 33, wherein the ring is a D-ring.

35. The sling of claim 1, further comprising a back strap joining the pouch to the shoulder strap and the locking strap.

36. The sling of claim 35, wherein the shoulder strap joins the locking strap and the back strap at a triangle buckle.

37. The sling of claim 36, wherein at least one of the shoulder strap or the back strap or the lock strap is adjustable about the triangle buckle.

38. The sling of claim 1, wherein the pouch includes an inelastic strip positioned along a bottom region of the pouch forming a flat platform positioned to support the elbow.

39. A sling for supporting an arm comprising
a pouch for receiving a user's arm, the pouch having a front panel and a back panel, wherein at least one panel has an elastic component,
an inelastic strip forming a substantially flat platform wider than the width of a stitch and being positioned along a bottom region of the pouch, and
a shoulder strap configured to attach to the front and back panels that supports the weight of the user's arm
a locking strap, and a locking assembly comprising a first connection point attached to the pouch for connecting the shoulder strap to pouch, and a second connection point positioned along the shoulder strap to be disposed between the first connection point and the user's shoulder for connecting the locking strap to the shoulder strap.

40. A sling for supporting an arm comprising
a pouch for receiving a user's arm and having a front panel and a back panel, each of the front panel and the back panel having an external surface and an internal surface and each of the front panel and the back panel having an attachment strip extending across its respective external surface,
a shoulder strap having a front portion and a rear portion,
a locking strap that extends under the user's arm
a support pad having a first surface for resting against the user's torso, a second surface facing away from the user's torso, and an attachment strip extending across the second surface
a locking strap, and a locking assembly comprising a first connection point attached to the pouch for connecting the shoulder strap to the pouch, and a second connection point positioned along the shoulder strap to be disposed between the first connection point and the user's shoulder for connecting the locking strap to the shoulder strap.

41. The sling of claim 40, wherein the shoulder strap has an adjustable length.

42. The sling of claim 40 comprising a hand strap attached to an interior face of the front panel along the distal portion of the pouch and positioned to fit between the user's thumb and forefinger when the sling is applied to the arm.

43. The sling of claim 40 comprising an inelastic strip positioned along a bottom region of the pouch.

44. The sling of claim 40, wherein the shoulder strap is configured for positioning on a shoulder opposite of the arm being supported.

45. The sling of claim 40, wherein the attachment strip extending across the second surface of the support pad attaches to the attachment strip located on the external surface of the front panel of the pouch.

46. The sling of claim 40, wherein the attachment strip extending across the second surface of the support pad attaches to the attachment strip located on the external surface of the back panel of the pouch.

\* \* \* \* \*

UNITED STATES PATENT AND TRADEMARK OFFICE
CERTIFICATE OF CORRECTION

PATENT NO. : 7,749,179 B2  Page 1 of 1
APPLICATION NO. : 11/282330
DATED : July 6, 2010
INVENTOR(S) : Hargrave et al.

It is certified that error appears in the above-identified patent and that said Letters Patent is hereby corrected as shown below:

In the Claims:

In Claim 39, column 14, lines 4-5, delete "configured to attach to the front and back panels"

In Claim 39, column 14, line 5, please add -- , -- after arm

In Claim 39, column 14, line 8, please add -- the -- before pouch

Signed and Sealed this

Fifth Day of October, 2010

David J. Kappos
*Director of the United States Patent and Trademark Office*